United States Patent

Giusti et al.

[11] Patent Number: 4,831,201
[45] Date of Patent: May 16, 1989

[54] PROCESS FOR OLIGOMERIZING LIGHT OLEFINS OR MIXTURES THEREOF

[75] Inventors: Aldo Giusti, Lucca; Stefano Gusi, Bologna; Giuseppe Bellussi, Piacenza; Vittorio Fattore, San Donato Milanese, all of Italy

[73] Assignees: Eniricerche S.P.A.; AGIP S.P.A., both of Milan, Italy

[21] Appl. No.: 189,646

[22] Filed: May 3, 1988

[30] Foreign Application Priority Data

May 5, 1987 [IT] Italy ............................... 20369 A/87

[51] Int. Cl.$^4$ ............................ C07C 2/04; C07C 2/12
[52] U.S. Cl. ................................... 585/531; 585/530; 423/326
[58] Field of Search ............... 585/531, 530, 520, 524; 423/326

[56] References Cited

U.S. PATENT DOCUMENTS 4,554,396  11/1985  Chang et al. ..................... 585/533

Primary Examiner—H. M. S. Sneed
Assistant Examiner—Chung K. Pak
Attorney, Agent, or Firm—Birch, Stewart, Kolasch & Birch

[57] ABSTRACT

A process is disclosed for oligomerizing light olefins or mixtures thereof, which consists in reacting said olefins, possibly diluted with an inert gas, by means of synthetic zeolites containing oxides of silicon, titanium and iron, having, in their calcined and anhydrous state, the following empirical formula:

$$pHFeO_2 \cdot qTiO_2 \cdot SiO_2,$$

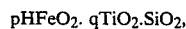

wherein p has a value larger than zero and smaller than, or equal to, 0.050 and g has a value larger than zero and smaller than, or equal to 0.025, and the H$^+$ of HFeO$_2$ can be at least partially substitutable or substituted with cations.

8 Claims, No Drawings

PROCESS FOR OLIGOMERIZING LIGHT OLEFINS OR MIXTURES THEREOF

BACKGROUND OF THE INVENTION

The present invention relates to a process for oligomerizing the light olefins by means of a synthetic, crystalline, porous material.

Several processes for oligomerizing the olefins are known, which use synthetic zeolites as catalysts.

From U.S. Pat. Nos. 3,756,942; 3,760,024; 3,775,501; 3,827,968; 3,960,978; 4,021,502; 4,150,062 and 4,227,992 processes are known for producing high-octane gasolines by starting from olefins by means of zeolites of "ZSM" type, i.e., zeolites constituted by oxides of silicon and aluminum.

From U.S. Pat. No. 4,554,396 the use is known as well, for said processes, of a zeolite constituted by oxides of silicon and iron.

The present Applicant has found that a synthetic zeolite containing oxides of silicon, titanium and iron is capable of oligomerizing the light olefins with a higher selectivity and a conversion than as obtained with the previously mentioned catalysts, with the temperature being the same.

SUMMARY OF THE INVENTION

The object of the present invention is a process for oligomerizing light olefins, or mixtures thereof, which consists in reacting said olefins, possibly diluted with an inert gas, by means of synthetic zeolites containing oxides of silicon, titanium and iron, having in their calcined and anhydrous state, the following empirical formula:

$$pHFeO_2 \cdot qTiO_2 \cdot SiO_2,$$

wherein p has a value larger than zero or smaller than, or equal to, 0.050 and q has a value larger than zero, and smaller than, or equal to, 0.025, and the $H^+$ of $HFeO_2$ can be at least partially substitutable, or substituted, with cations.

The transition from a cationic form to another cationic form can be carried out with the usual exchange processes known from the prior art.

The reaction of oligomerization is carried out at a temperature comprised within the range of from 220° to 350° C., preferably of from 230° to 320° C., under a pressure preferably comprised within the range of from 1 to 30 abs.atm., and at a space velocity WHSV comprised within the range of from 0.1 to 10 hours$^{-1}$, preferably of from 0.3 to 5 hours$^{-1}$.

The light olefins have a number of carbon atoms comprised within the range of from 2 to 10, preferably comprised within the range of from 2 to 4.

The products which are obtained by means of said process are above-all olefins and aromatic hydrocarbons containing from 5 to 20 carbon atoms.

DETAILED DESCRIPTION OF THE INVENTION

The above-defined synthetic zeolites of the present invention, containing oxides of silicon, titanium and iron were shown to be crystalline when tested by X-ray examination.

Such an examination was carried out by means of a powder diffractometer equipped with an electronic pulse-counting system, using CuK$\alpha$ radiation. For the computation of the intensity values, the heights of the peaks were measured, and the percent value of each of them relatively to the most intense peak was computed. The main reflections for the calcined and anhydrous product are characterized by the following d values (wherein d is the interplanar distance):

| d (Å) | Relative Intensity |
| --- | --- |
| 11.14 + 0.10 | vs |
| 9.99 + 0.10 | s |
| 9.74 + 0.10 | m |
| 6.36 + 0.07 | mw |
| 5.99 + 0.07 | mw |
| 4.26 + 0.05 | mw |
| 3.86 + 0.04 | s |
| 3.82 + 0.04 | s |
| 3.75 + 0.04 | s |
| 3.72 + 0.04 | s |
| 3.65 + 0.04 | m |
| 3.05 + 0.02 | mw |
| 2.99 + 0.02 | mw |

(vs = very strong;
s = strong;
m = medium;
mw = medium-weak).

Said zeolites used by us showed an I.R. spectrum characterized by at least the following most representative values of wn (wherein wn is the wave number):

| wn (cm$^{-1}$) | Relative Intensity |
| --- | --- |
| 1220–1230 | w |
| 1080–1110 | s |
| 965–975 | mw |
| 795–805 | mw |
| 550–560 | m |
| 450–470 | ms |

(s = strong;
ms = medium-strong;
m = medium;
mw = medium-weak;
w = weak).

The preparation process in order to obtain said zeolites is characterized in that a derivative of silicon, a derivative of titanium, a derivative of iron and a nitrogenous organic base are reacted under hydrothermal conditions, with a molar ratio of $SiO_2/Fe_2O_3$ of the reactants higher than 50, preferably comprised within the range of from 150 to 600, a molar ratio of $SiO_2/TiO_2$ of the reactants higher than 5, preferably comprised within the range of from 15 to 25, a molar ratio of $H_2O/SiO_2$ of the reactants preferably comprised within the range of from 10 to 100, more preferably comprised within the range of from 30 to 50, possibly in the presence of one or more alkali or alkali-earth salts and/or hydroxides, with a molar ratio of $M/SiO_2$ (wherein M is the alkali or alkali-earth cation) of the reactants lower than 0.1, preferably lower than 0.01, or zero. In the empirical formula of the material, iron was put in $HFeO_2$ form, in order to evidence that the material is in $H^+$ form. When we speak in terms of the ratios of the various reactants, for iron the $Fe_2O_3$ form is used, in that it is more usual.

The derivative of silicon is selected from silica gel, silica sol and alkyl silicates, among which tetraethyl silicate is preferred; the derivative of titanium is selected from the salts, such as, e.g., the halides, and the organic derivatives of titanium such as, e.g., the alkyl titanates, preferably tetraethyl titanate; the derivative of iron is selected from the salts, such as, e.g., the halides and the nitrates, the hydroxides and the organic derivatives, such as, e.g., the alkoxides.

The nitrogenous organic base can be an alkylammonium hydroxide, preferably tetrapropylammonium hydroxide.

In case tetrapropylammonium hydroxide is used, the $TPA^+/SiO_2$ ratio (wherein TPA=tetrapropylammonium) of the reactants is comprised within the range of from 0.1 to 1, preferably of from 0.2 to 0.4. The reactants are made to react by operating at a temperature comprised within the range of from 100° to 200° C., preferably of from 160° to 180° C., at a pH comprised within the range of from 9 to 14, preferably of from 10 to 12, and for a timer period ranging from 1 hour to 5 days, preferably from 3 hours to 10 hours.

Titanium-iron-silicalite is recovered by filtration or centrifugation, is washed, dried, is calcined, preferably at 500°–600° C. for a time preferably comprised within the range of from 4 to 8 hours, and then it is exchanged into the acidic form according to processes known to those skilled in the art.

According to another form of practical embodiment, titanium-iron-silicalite can be bonded with amorphous oligomeric silica, with a molar ratio of oligomeric silica/titanium-iron-silicalite comprised within the range of from 5:95 to 20:80, wherein the crystals of titanium-iron-silicalite are bonded in the crystal lattice by means of Si—O—Si bonds, with the mass of the crystals of titanium-iron-silicalite with silica being in the form of microspheres having a diameter comprised within the range of from 5 to 1000 $\mu$m.

According to a further form of practical embodiment, the material obtained, as such or in the form of microspheres, can be pelletized or extruded according to the techniques known in the art, in order to obtain pellets or extrudates having the desired size, and then calcined up to temperatures preferably contained within the range of from 500° to 600° C.

Furthermore, to titanium-iron-silicalite, as such, or in bonded form, a support may be added, which is selected from more or less inert materials well known in the literature, such as aluminas, kaolins, silicas, and so forth, with the amounts of said support being comprised within the range of from 10 to 40% by weight, and preferably of from 15 to 35% by weight. Finally, the blend is fabricated and calcined.

The olefins used for the oligomerization reaction, comprised within the range of from $C_2$ to $C_{10}$, can be ethylene, propylene, 1-butene, cis and trans 2-butene, isobutene, and so forth, either as individual compounds, or as mixtures.

They can be furthermore used in pure form, or diluted with inert materials, such as nitrogen, methane, ethane, butane and other higher paraffins, and so forth, as well as with the portion of the reaction products.

The unreacted olefins can be separated by means of the conventional methods, and recycled.

The reaction of oligomerization can be carried out over a fixed bed or over a fluidized bed, at temperatures, pressures, flow rates of the reactants, which may vary within a wide range, and depend on the particular mixture fed to the reactor.

In order to better illustrate the scope of the present invention, the following examples are reported, the same, however are not to be construed as being limitative of the present invention.

Example 1

This example illustrates the preparation of titanium-iron-silicalite.

0.65 g of $Fe(NO_3)_3.9H_2O$ is dissolved in water, and from the solution iron hydroxide is precipitated by adding ammonium hydroxide. The precipitate is filtered off, and is washed by re-dispersion in cold water and filtration until the filtrate turns to neutral. The damp hydroxide is then dissolved in 54 g a solution of tetrapropylammonium hydroxide at 18.7% by weight. Separately, 2.28 g of tetraethylorthotitanate is dissolved in 41.6 g of tetraethylsilicate, and this solution is added to the previous one with stirring.

The total mass is kept heated at 50°–60° C., always with stirring, until a single-phase solution is obtained, then 100 cc of water is added.

The obtained solution is charged to an autoclave, and is heated under its autogenous pressure at 170° C. for 4 hours.

The product is discharged and centrifuged and washed twice by re-dispersion and centrifugation, and is then dried 1 hour at 120° C., and then calcined for 4 hours at 550° C. in air.

The obtained product has a molar ratio of $SiO_2/Fe_2O_3=394$, and a molar ratio of $SiO_2/TiO_2=48$.

Example 2

By the same modalities as shown in Example 1, a further preparation is carried out, for which in Table 1 the molar compositions of the reactant mixtures and of the obtained products, as they result from the chemical analysis, are reported.

TABLE 1

| Example | Composition of the Reaction Mixture | | | | Composition of the Products | |
|---|---|---|---|---|---|---|
| | $SiO_2/TiO_2$ | $SiO_2/Fe_2O_3$ | $TPA^+/SiO_2$ | $H_2O/SiO_2$ | $SiO_2/TiO_2$ | $SiO_2/Fe_2O_3$ |
| 1 | 20 | 250 | 0.25 | 40 | 48 | 394 |
| 2 | 20 | 800 | 0.25 | 40 | 46 | 573 |

Example 3

To a tubular reactor of steel, with an inner diameter equal to 10 mm, heated by means of an electrical oven, 1.5 cc of titanium-iron-silicalite—prepared according to Example 1 ($SiO_2/Fe_2O_3=394$; $SiO_2/TiO_2=48$), and submitted to granulation and sieving for collecting the fraction of from 20 to 40 mesh ASTM—is charged.

The catalyst is heated under nitrogen up to the reaction temperature, and propylene is then fed. The reaction products are analysed by gas-chromatography, with an on-line drawing being carried out.

The process conditions and the results obtained are the following:

| | |
|---|---|
| Temperature = | 260° C. |
| Pressure = | 1 abs.atm |
| WHSV = | 0.6 hours$^{-1}$ |
| $C_3H_6/N_2$ ratio = | ½ (volume/volume) |
| $C_3H_6$ conversion = | 92% (weight/weight) |
| Yield of $C_5$ and higher olefin oligomers = | 76% (weight/weight) |

-continued

| Selectivity to | % (weight/weight) |
|---|---|
| $C_2 =$ | 0.1 |
| $C_3H_8 =$ | 0.7 |
| $C_4 =$ | 16 |
| $C_5 =$ | 21 |
| $C_6 =$ | 19 |
| $C_7$ and higher $=$ | 43 |

In this, and in the following, examples WHSV is defined as:

$$\frac{\text{weight of fed olefin}}{\text{weightr of catalyst}} \times \frac{1}{h}$$

Example 4

To the same reactor as of Example 3, 1.5 cc is charged of titanium-iron-silicalite prepared according to Example 2 ($SiO_2/Fe_2O_3 = 573$; $SiO_2/TiO_2 = 46$), ground and sieved so as to collect the fraction of 20–40 mesh ASTM.

The catalyst is heated under nitrogen up to the reaction temperature, and then propylene is fed. The analysis of the products is carried out on-line by gas-chromatography.

The process conditions and the results obtained are the following:

| | |
|---|---|
| Temperature = | 260° C. |
| Pressure = | 1 abs.atm |
| WHSV = | 0.6 hours$^{-1}$ |
| $C_3H_6/N_2$ ratio = | ½ (volume/volume) |
| $C_3H_6$ conversion = | 80% (weight/weight) |
| Yield of $C_5$ and higher = | 66% (weight/weight) |
| olefin oligomers | |
| Selectivity to | % (weight/weight) |
| $C_2 =$ | 0.1 |
| $C_3H_8 =$ | 0.6 |
| $C_4 =$ | 17 |
| $C_5 =$ | 20 |
| $C_6 =$ | 19 |
| $C_7$ and higher $=$ | 43 |

Example 5

To the same reactor of Example 3, 1.5 cc is charged of titanium-iron-silicalite prepared according to Example 2 ($SiO_2/Fe_2O_3 = 573$; $SiO_2/TiO_2 = 46$) and of a size of 20–40 mesh ASTM.

The catalyst is heated under nitrogen up to the reaction temperature, and then propylene is fed. The reaction products are analysed on-line by gas-chromatography.

The process conditions and the results obtained are the following:

| | |
|---|---|
| Temperature = | 310° C. |
| Pressure = | 1 abs.atm |
| WHSV = | 0.6 hours$^{-1}$ |
| $C_3H_6/N_2$ ratio = | ½ (volume/volume) |
| $C_3H_6$ conversion = | 95% (weight/weight) |
| Yield of $C_5$ and higher = | 74% (weight/weight) |
| olefin oligomers | |
| Selectivity to | % (weight/weight) |
| $C_2 =$ | traces |
| $C_3H_8 =$ | 0.8 |
| $C_4 =$ | 21 |
| $C_5 =$ | 25 |
| $C_6 =$ | 18 |
| $C_7$ and higher $=$ | 35 |

Example 6

To the same reactor of Example 3, 1.5 cc is charged of titanium-iron-silicalite prepared according to Example 1 ($SiO_2/Fe_2O_3 = 394$; $SiO_2/TiO_2 = 48$) (granulometry: 20–40 mesh ASTM).

The catalyst is heated under nitrogen up to the reaction temperature, and then 1-butene is fed. The analysis is carried out on-line by gas-chromatography.

The process conditions and the results obtained are the following:

| | |
|---|---|
| Temperature = | 300° C. |
| Pressure = | 1 abs.atm |
| WHSV = | 0.6 hours$^{-1}$ |
| 1-Butene/$N_2$ ratio = | ½ (volume/volume) |
| 1-Butene conversion = | 88% (weight/weight) |
| Yield of $C_5$ and higher = | 41% (weight/weight) |
| olefin oligomers | |
| Selectivity to | % (weight/weight) |
| $C_2 =$ | traces |
| $C_3H_8 =$ | 3 |
| $C_4 =$ | 51 |
| $C_5 =$ | 9 |
| $C_6 =$ | 8 |
| $C_7$ and higher $=$ | 29 |

Example 7

To the same reactor of Example 3, 1.5 cc is charged of titanium-iron-silicalite prepared according to Example 2 ($SiO_2/Fe_2O_3 = 573$; $SiO_2/TiO_2 = 46$) (granulometry: 20–40 mesh ASTM).

The catalyst is heated under nitrogen up to the reaction temperature, and then 1-butene is fed. The analyses are carried out on-line by gas-chromatography.

The process conditions and the results obtained are the following:

| | |
|---|---|
| Temperature = | 310° C. |
| Pressure = | 1 abs.atm |
| WHSV = | 0.6 hours$^{-1}$ |
| 1-Butene/$N_2$ ratio = | ½ (volume/volume) |
| 1-Butene conversion = | 64% (weight/weight) |
| Yield of $C_5$ and higher = | 47% (weight/weight) |
| olefin oligomers | |
| Selectivity to | % (weight/weight) |
| $C_2 =$ | traces |
| $C_3H_8 =$ | 6 |
| $C_4 =$ | 21 |
| $C_5 =$ | 22 |
| $C_6 =$ | 16 |
| $C_7$ and higher $=$ | 35 |

(Comparative) Example 8

To the same reactor of Example 3, 1.5 cc is charged of a zeolite constituted by oxides of silicon and iron, with an $SiO_2/Fe_2O_3$ ratio = 189 (granulometry of 20–40 mesh ASTM).

The catalyst is heated under nitrogen up to the reaction temperature, and then propylene is fed. The analyses are carried out on-line by gas-chromatography.

The process conditions and the results obtained are the following:

| | |
|---|---|
| Temperature = | 310° C. |
| Pressure = | 1 abs.atm |
| WHSV = | 0.6 hours$^{-1}$ |
| $C_3H_6/N_2$ ratio = | ½ (volume/volume) |
| $C_3H_6$ conversion = | 94% (weight/weight) |
| Yield of $C_5$ and higher = olefin oligomers | 71% (weight/weight) |
| Selectivity to | % (weight/weight) |
| $C_2$ = | 0.7 |
| $C_3H_8$ = | 0.9 |
| $C_4$ = | 23 |
| $C_5$ = | 20 |
| $C_6$ = | 14 |

One can observe that in order to achieve high conversion levels, similar to those as obtained in Example 3, the process should be run at 310° C. and the yield of $C_5$ and higher hydrocarbons is lower than of analogous Example 3.

(Comparative) Example 9

To the same reactor of Example 3, 1.5 cc is charged of a ZSM-5 zeolite prepared according to Example 1 of U.S. Pat. No. 3,702,886.

The catalyst is heated up to the reaction temperature, and then propylene is fed. The process conditions and the results obtained are the following:

| | |
|---|---|
| Temperature = | 260° C. |
| Pressure = | 1 abs.atm |
| WHSV = | 0.6 hours$^{-1}$ |
| $C_3H_6/N_2$ ratio = | ½ (volume/volume) |
| $C_3H_6$ conversion = | 63% (weight/weight) |
| Yield of $C_5$ and higher = olefin oligomers | 48% (weight/weight) |
| Selectivity to | % (weight/weight) |
| $C_2$ = | 0.2 |
| $C_3H_8$ = | 0.3 |
| $C_4$ = | 23 |
| $C_5$ = | 23 |
| $C_6$ = | 20 |
| $C_7$ and higher = | 33 |

One can observe that the activity and selectivity to $C_5$ and higher olefin oligomers for these catalysts are considerably lower than of Example 3.

We claim:

1. A process for oligomerizing light olefins having 2 to 10 carbon atoms individually, or mixtures thereof, characterized in that said olefins, with or without being diluted with an inert gas, are reacted with a synthetic zeolite containing oxides of silicon, titanium and iron, having in its calcined and anhydrous state, the following empirical formula:

$$pXFeO_2.qTiO_2.SiO_2,$$

wherein p has a value larger than zero but smaller than or equal to 0.050, and q has a value larger than zero but smaller than or equal to 0.025, and X being H+ or other cations, at a temperature of from about 220° to 350° C., and at a weight hourly space velocity of from about 0.1 to 10 hours$^{-1}$.

2. The process according to claim 1, wherein the oligomerizing reaction is carried out at a temperature of from about 230° to 320° C.

3. The process according to claim 1, wherein the oligomerizing reaction is carried out at a weight hourly space velocity of from about 0.3 to 5 hours$^{-1}$.

4. The process according to claim 1, wherein the oligomerizing reaction is carried out under a pressure of from about 1 to 30 absolute atmospheres.

5. The process according to claim 1, wherein said olefins have a number of carbon atoms of from 2 to 4.

6. The process according to claim 1, wherein the synthetic zeolite is bonded with amorphous oligomeric silica, with a molar ratio of said oligomeric silica to said zeolite being from about 5:95 to 20:80, wherein the crystals of said zeolite are mutually bonded in the crystal lattice by Si—O—Si bonds, with silica being in the form of microspheres having a diameter in the range of from about 5 to 1000μm.

7. The process according to claim 1 or 6, wherein a support material is added to said synthetic zeolite or to said synthetic zeolite bonded to said amorphous silica.

8. The process according to claim 7 wherein said support material is alumina, kaolin or silica.

* * * * *